United States Patent
Amitai

[19]

[11] Patent Number: 5,980,960
[45] Date of Patent: Nov. 9, 1999

[54] SAMPLER APPLICATOR HAVING A STRETCHY LAYER

[75] Inventor: Nathan Amitai, Closter, N.J.

[73] Assignee: Arcade, Inc., Chatanooga, Tenn.

[21] Appl. No.: 08/843,316

[22] Filed: Apr. 25, 1997

[51] Int. Cl.⁶ ............... A46B 5/04; A46B 3/00; A45D 40/24; B65D 85/74
[52] U.S. Cl. ............ 426/115; 426/112; 206/484; 206/581; 206/823; 15/104.94; 132/320; 401/7; 602/48; 604/308
[58] Field of Search .................. 426/115, 112, 426/106; 206/484, 581, 823; 15/104.93, 104.94; 132/320; 602/48; 604/304, 308; 401/7

[56] References Cited

U.S. PATENT DOCUMENTS

| | | |
|---|---|---|
| 1,334,346 | 3/1920 | Boehm .................................. 426/115 |
| 2,002,144 | 5/1935 | Heaton . |
| 2,419,896 | 4/1947 | Hobelmann . |
| 2,511,557 | 6/1950 | Arnold . |
| 3,635,567 | 1/1972 | Richardson, Jr. . |
| 3,640,629 | 2/1972 | Geiser . |
| 3,647,305 | 3/1972 | Baker et al. . |
| 4,596,481 | 6/1986 | Tanaka . |
| 4,648,506 | 3/1987 | Campbell ................................ 426/115 |
| 4,739,778 | 4/1988 | Christie . |
| 4,752,496 | 6/1988 | Fellows et al. . |
| 4,755,433 | 7/1988 | Patel et al. . |
| 4,838,851 | 6/1989 | Shabo . |
| 4,890,872 | 1/1990 | Parrotta et al. . |
| 4,908,252 | 3/1990 | Carnahan et al. . |
| 4,998,621 | 3/1991 | Meehan . |
| 5,072,831 | 12/1991 | Parrotta et al. . |
| 5,106,629 | 4/1992 | Cartmell et al. . |
| 5,161,688 | 11/1992 | Muchin . |
| 5,348,153 | 9/1994 | Cole ....................................... 206/361 |
| 5,396,913 | 3/1995 | Wallschlaeger . |
| 5,445,821 | 8/1995 | Brown et al. . |
| 5,524,764 | 6/1996 | Kaufman et al. . |
| 5,538,022 | 7/1996 | Bennett . |
| 5,715,849 | 2/1998 | Vanbraekel . |

Primary Examiner—David Lacey
Assistant Examiner—Hao Mai
Attorney, Agent, or Firm—Pennie & Edmonds LLP

[57] ABSTRACT

A sampler device for applying sample material having a supporting base with a hole through its width. A stretchy layer, such a latex, is affixed to the base to cover the hole. A cover protects sample material deposited on the stretchy layer. After removing the cover, a user inserts a finger through the hole, stretches the stretchy layer into an applicator shape, and applies or consumes the sample material.

21 Claims, 3 Drawing Sheets

SAMPLER APPLICATOR HAVING A STRETCHY LAYER

FIELD OF THE INVENTION

The present invention relates generally to a device for sampling and applying sample material, and more specifically to a sampler having sample material on a stretchy layer which attractively displays sample material and may be deformed by a user into a shape suitable for applying or consuming the sample material.

BACKGROUND OF THE INVENTION

Several types of samplers are known which allow consumers to test a product before purchasing a full size container. Often, businesses such as those in the cosmetic industry obtain new customers by distributing samples of their products to potential customers. Samplers are commonly available in retail stores or are distributed in magazines or through the mail.

The prior art includes flat samplers suited for stacking, storing in a small volume, or mailing. U.S. Pat. No. 5,072,831 to Parrotta et al., for example, provides a layer of sample material on a flat, paper-stock sheet that is coated with a barrier layer. A removable, transparent cover protects the sample material and allows consumers to see the sample before opening the sampler. To apply the sample material, a user must first rub it off the sampler with her finger.

This manner of application is both messy and inconvenient. Moreover, the sample material may become contaminated by the finger. Users' fingers become dirtied, and samples can stain clothes if the applying finger is not thoroughly cleaned. Also, if a user desires to apply more than one sample, she must either employ different fingers to avoid mixing samples, or wipe her applying finger repeatedly.

U.S. Pat. No. 4,739,778 to Christie, on the other hand, requires no finger contact with the sample material. The patent shows a product-sampling dispenser molded to provide a pod area that holds a sample, such as lipstick. To apply the sample, the user pulls back a cover sheet and pops the pod either by squeezing the back of the pod with her finger, or by bending the pod in half. The user may then squeeze the pod to extract the sample and apply the lipstick directly to her lips.

The applicator disclosed in this patent, however, has an awkward shape for applying certain kinds of sample materials, and usually will not have the shape of a regular size applicator. The lipstick embodiment described shows a user spreading a sample on her lips from the relatively flat applicator, whereas lipstick is normally and more readily applied from an elongated and rounded applicator.

Other disclosures teach single-use applicators with more convenient shapes. For example, U.S. Pat. No. 4,838,851 to Shabo features packaged handles and applicator swabs for applying a small amount of liquid to eyelids. The swabs are pre-wet with a liquid. In this teaching, the appearance of the sample itself cannot be readily displayed. The soaked swab, for instance, creates a different visual impression than the sample material would in a transparent container by itself. Also, the swab, having been selected for applying liquids, is not the type of applicator normally used for certain types of sample material; nor is it the most convenient. For example, lipstick would more naturally be sampled with differently shaped applicators.

U.S. Pat. No. 5,538,022 to Bennett discloses an applicator shaped like a tube of lipstick. A preselected amount of sample lipstick is deposited on the applicator. This sample may be contained in a disposable container, permanent dispenser, or within the applicator.

Having the shape of a normal lipstick tube, the disclosed device presents no space savings for a retailer over a full size lipstick. This same shape precludes space-efficient sampler stacking as well as mailing samplers in a flat envelope or magazine.

Other patents teach finger-sheath applicators.

U.S. Pat. Nos. 2,002,114 to Heaton and 2,551,557 to Arnold show soft, flexible finger-cots for applying lipstick. The Arnold patent's cot is made from soft rubber. Both finger cots have inflexible rings at their bases that help maintain the cots' shape and facilitates the insertion of a finger.

U.S. Pat. No. 5,524,764 to Kaufman et al. shows a transparent, essentially flat package having a number of compartments. One compartment holds a single-use supply of toothpaste. Another holds a latex sheath with an abrasive absorbent-material to be worn on a finger for applying the toothpaste. U.S. Pat. No. 2,419,896 to Hobelmann discloses a single-use dentifrice-applicator folded from paper with dentifrice on its surface.

The above finger sheaths maintain their basic shape when not in use. The cots with rings at their bases are meant as reusable applicators and do not lend themselves to stacking or shipping. The sheath of the Kaufman patent is merely a piece of shaped latex and has no supporting base to assist its placement on or removal from a finger. The paper applicator of the Hobelmann patent fails to conform to the wearer's finger and provides a relatively flat applicator-surface shaped inconveniently for applying certain sample-substances, such as lipstick.

Other known samplers are designed for sampling food. These generally suffer from the disadvantage that they require a utensil such as a spoon to consume the sample, and the sampler size and shape is limited by the need to provide such a utensil. A user may scoop the sample with a finger, but may then contaminate the sample material.

The prior art does not provide a normally flat sampler in which sample material may be directly displayed in an appealing, flat form and that may be deformed by the user into a convenient applicator shape for use without contaminating the sample material with a finger or other object.

SUMMARY OF THE INVENTION

A sampler device according to the invention comprises a base with a hole extending through its thickness. A stretchy layer, such as latex or rubber, is affixed to the base so that it covers the hole. Sample material is deposited onto the stretchy layer in alignment with the hole. A removable cover protects the sample material.

To apply the sample material, a user stretches and shapes the stretchy layer by pressing her finger through the hole. She may then apply the sample material to a surface appropriate to the type of sample contained. If the sample material is food, the user may then consume it. This sampler device practically eliminates contact with, and therefore contamination of, the sample material.

BRIEF DESCRIPTION OF THE DRAWINGS

Reference is next made to a brief description of the drawings, which are intended to illustrate a first embodiment and a number of alternative embodiments of the sampler device according to the present invention. The drawings and detailed descriptions which follow are intended to be merely illustrative and are not intended to limit the scope of the invention as set forth in the appended claims.

DETAILED DESCRIPTION OF THE PREFERRED EMBODIMENTS

Figure 1:
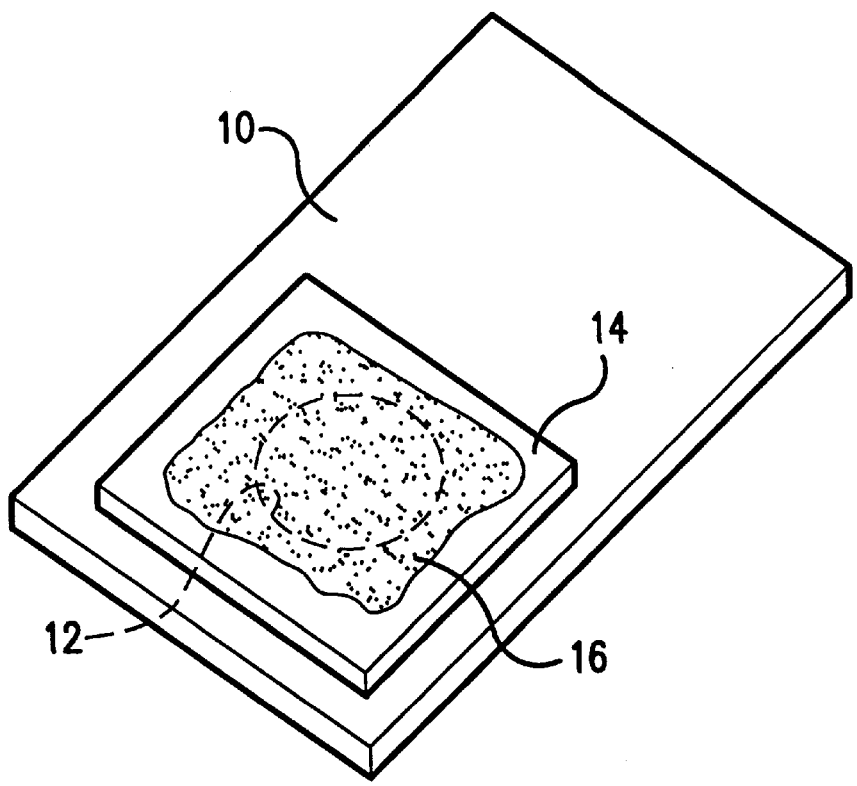
FIG. 1 is a perspective view of a sampler device according to the present invention.

FIG. 1 shows a preferred embodiment of a sampler device according to the invention. The sampler device comprises a preferably flat base 10 forming a support structure for the sampler device. Base 10 defines a hole 12 extending through the base 10. Hole 12 is large enough for a user to insert her finger or another object therein.

A stretchy or elastic layer 14 covers the hole 12 and is secured to the base 10 around the circumference of the hole 12. Preferably, the stretchy layer 14 is bonded or cemented to the base 10. Also, preferred materials for the stretchy layer 14 are elastic. Most preferably, the stretchy layer 14 is made from latex or rubber, but other materials may be used. Depending on the type of sample material 16 used and the type of application desired, the stretchy layer 14 also may be porous or meshlike to enhance bonding with the sample material 16.

A coat of sample material 16 is deposited on the stretchy layer 14 in alignment with the hole 12. In the preferred embodiment, the sample material 16 is disposed on a side of the stretchy layer 14 opposite the hole 12. The sample material 16 may be deposited by any known method including by coating, printing, or dispensing processes. Examples of such processes are silk screening and spraying. In the case of a single-use sampler device, an amount of sample material 16 sufficient for one application is applied to the sampler device.

Figure 2:
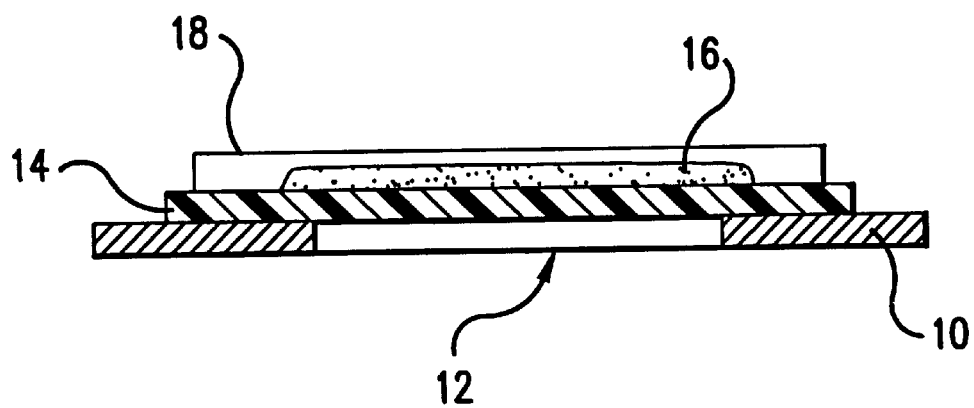
FIG. 2 shows a cross-section of a sampler device with a cover according to the invention.

FIG. 2 shows a cross section of an embodiment of the invention with a removable cover 18 protecting the sample material 16. The cover 18 is preferably transparent, although this need not be the case, so a user may see the sample material 16 itself and form visual impressions of qualities of the sample material 16 such as its color. This feature permits users at a retail store to quickly pick a number of samples in which they are interested. A logo or other advertising material may also be printed on the cover 18.

Figure 3:
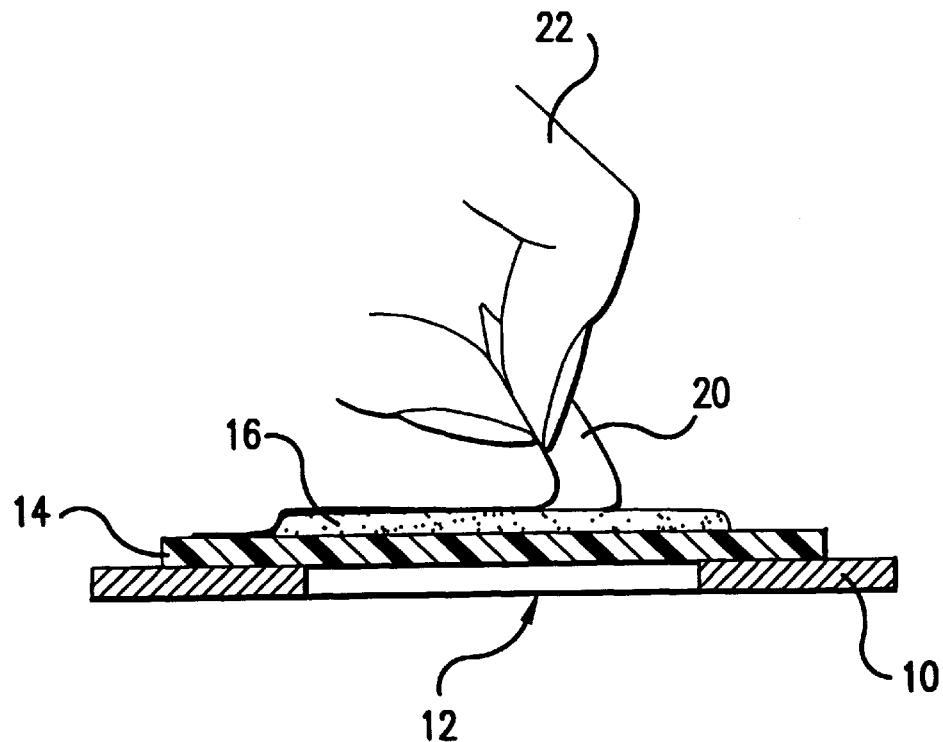
FIG. 3 shows an embodiment of the invention with a peelable film cover.

The cover 18 shown in FIG. 2 is affixed to the stretchy layer 14. The cover 18 may otherwise be fixed to base 10 or another part of the sampler device. As shown in FIG. 3, a cover 20 may comprise a film placed over the surface of the sample material 16 and adhered to part of the surface of the stretchy layer 14. This cover 20 may be peeled from the sampler device before use, as illustrated. Alternative covers include a sealed plastic bag enclosing the entire sampler device, and other covers commonly known in the art.

Figure 4:
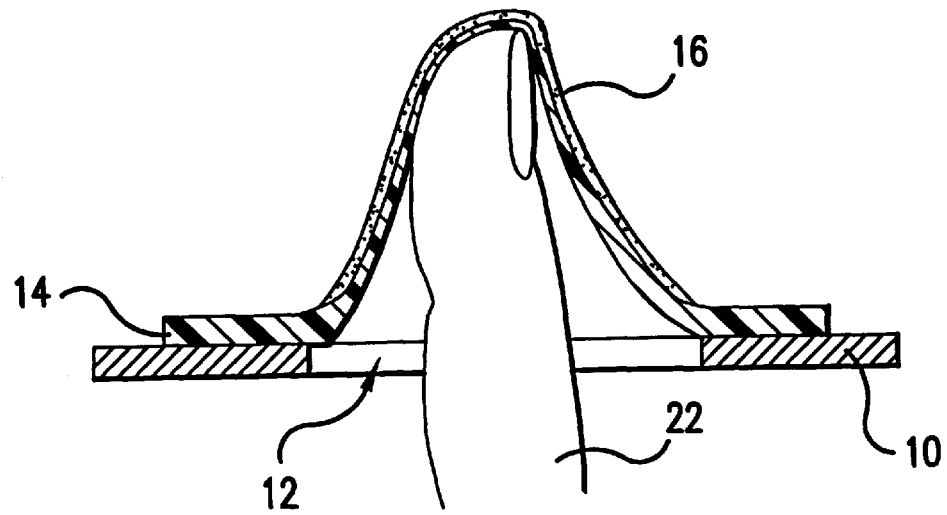
FIG. 4 is a cross-sectional view of an embodiment of the invention just prior to use.

FIG. 4 displays a sampler device whose cover 18 or 20 has been removed. To apply the sample material 16, a user inserts her finger 22 into the hole 12 in base 10. While holding base 10, the user pushes against the underside of the stretchy layer 14. This action deforms the stretchy layer 14, together with the sample material 16 it holds, into a shape suitable for applying the sample material 16 to an appropriate object or for consuming it. Base 10 is preferably manufactured from materials that can withstand the stretching of the stretchy layer 14. Acceptable materials include paperboard or plastics.

By varying the depth and direction with which the user inserts her finger 22, she may select the most convenient applicator shape of the stretchy layer 14 according to the type of sample material 16 to be applied. This selected shape provides the sampler device of the invention with versatility of use. As a result, a wide range of sample materials 16 may be incorporated into the present invention. For example, sample material 16 may be a cosmetic which includes any external application intended to beautify or improve the complexion, skin, or hair. Examples of cosmetics include lipsticks, powders, foundations, mascaras, blushes, and eyeshadows. Other materials also may be incorporated into the present invention such as foods, paints, and crayons. In the case of foods, a user may apply the sample material 16 to his or her tongue or other part of the user's mouth for its consumption. In other words, the sampler device may be used as a lollipop.

Figure 5:
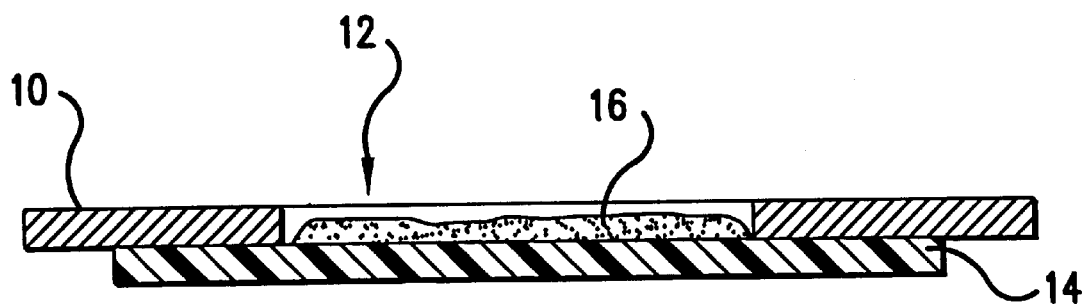
FIG. 5 shows a cross-section of an embodiment having sample material disposed on the same side as a base.

FIG. 5 shows a further embodiment of the present invention in which the sample material 16 is on the side of the stretchy layer 14 that faces the hole 12 in base 10. The sample material 16 in this embodiment is partially protected from deformation by the base 10, and the resulting sampler device can by thinner than in previous embodiments disclosed because the sample material 16 and the base 10 are not stacked. To apply or consume the sample material 16, the user employs a technique as described above, except that the user must push the stretchy layer 14 and the sample material 16 through the hole 12.

The sampler device according to the present invention provides the advantages of flat samplers. The color and texture of the sample material 16 is displayed on a visually attractive flat surface. If the sample material 16 is printed onto the stretchy layer 14, appealing designs or logos are achievable. Also, the sampler devices of the present invention occupy little storage and packaging space.

In an alternative embodiment, the sampler device and its hole 12 are adapted to receive an object other than a user's finger. The hole 12, for instance, may be shaped to receive a pen or other elongate object.

These variations are offered by way of example and not limitation, as it will be readily apparent to those in the art that other variations of this sampler device are possible which fall within the scope of the appended claims.

What is claimed:

1. A sampler device comprising:
   a support base;
   a stretchy layer secured to the support base so as to be in a flat position; and
   sample material deposited an the stretchy layer, wherein the stretchy layer is positioned on the support base so as to be adapted to be stretched away from the support base and out of the flat position for application or consumption of the sample material.

2. The sampler device of claim 1, wherein the base is flat.

3. The sampler device of claim 1, wherein the base is made from paperboard.

4. The sampler device of claim 1, wherein the support base has an opening that extends completely therethrough, wherein the stretchy layer covers the opening, and wherein the sample material is disposed on the stretchy layer in alignment with the opening.

5. The sampler device of claim 4, wherein the sample material is disposed on a side of the stretchy layer opposite the opening.

6. The sampler device of claim 4, wherein the sample material is disposed on a side of the stretchy layer facing the opening.

7. The sampler device of claim 4, wherein the opening is adapted for inserting a finger therethrough for applying pressure to the stretchy layer.

8. The sampler device of claim 4, wherein the stretchy layer is attached to the support base around the opening.

9. The sampler device of claim 1, wherein the stretchy layer is elastic.

10. The sampler device of claim 9, wherein the stretchy layer is made from an elastomer.

11. The sampler device of claim 9, wherein the elastic comprises an elastomer selected from the group consisting of latex and rubber.

12. The sampler device of claim 1, further comprising a cover for protecting the sample material, the cover being removably associated to the stretchy layer.

13. The sampler device of claim 12, wherein the cover is a peelable film.

14. The sampler device of claim 12, wherein the cover encloses the stretchy layer and the sample material.

15. The sampler device of claim 1, wherein the sample material is coated onto the stretchy layer.

16. The sampler device of claim 1, wherein the sample material is printed onto the stretchy layer.

17. The sampler device of claim 1, wherein the sample material is dispensed onto the stretchy layer.

18. The sampler device of claim 1, wherein the sample material is a cosmetic.

19. The sampler device of claim 1, wherein the sample material is a food.

20. The sampler device of claim 1, wherein the sample material is paint.

21. A sampler device for applying sample material on a surface, the sampler device comprising:

a flat, support base having a hole adapted for inserting a finger therethrough;

a stretchy layer covering the hole and having a back and a front, the back being secured to the support base circumferentially around the hole so as to be in a flat position;

a sample material coating on the front of the stretchy layer opposite the hole; and a detachable cover for protecting the sample material coating, wherein the stretchy layer may be deformed to a shape suited for applying or consuming the sample material by inserting the finger through the hole, thereby applying pressure to the back of the stretchy layer and stretching the stretchy layer away from the base and out of the flat position.

* * * * *